(12) United States Patent
Fu et al.

(10) Patent No.: US 11,740,143 B2
(45) Date of Patent: Aug. 29, 2023

(54) FLEXIBLE PRESSURE SENSOR ARRAY AND METHOD FOR FABRICATING THE SAME

(71) Applicant: Nano and Advanced Materials Institute Limited, Hong Kong (CN)

(72) Inventors: Li Fu, Hong Kong (CN); Tao Xu, Hong Kong (CN); Yam Chong, Hong Kong (CN)

(73) Assignee: Nano and Advanced Materials Institute Limited, Hong Kong (CN)

( * ) Notice: Subject to any disclaimer, the term of this patent is extended or adjusted under 35 U.S.C. 154(b) by 107 days.

(21) Appl. No.: 17/302,983

(22) Filed: May 18, 2021

(65) Prior Publication Data

US 2021/0372866 A1    Dec. 2, 2021

Related U.S. Application Data

(60) Provisional application No. 62/704,769, filed on May 28, 2020.

(51) Int. Cl.
*G01L 1/18* (2006.01)
*D06P 5/30* (2006.01)

(52) U.S. Cl.
CPC .................. *G01L 1/18* (2013.01); *D06P 5/30* (2013.01); *D10B 2401/18* (2013.01)

(58) Field of Classification Search
CPC .................................. G01L 1/18; G01L 1/205
See application file for complete search history.

(56) References Cited

U.S. PATENT DOCUMENTS

| | | | |
|---|---|---|---|
| 8,161,826 B1* | 4/2012 | Taylor | A47C 27/082 73/862.041 |
| 8,925,393 B2* | 1/2015 | Cannard | D04B 1/14 73/862.041 |
| 9,032,804 B2* | 5/2015 | Granado | G01L 9/06 73/700 |
| 9,271,665 B2* | 3/2016 | Sarrafzadeh | A61B 5/7278 |
| 9,349,911 B2* | 5/2016 | Lau | H01L 27/1214 |
| 9,371,979 B2* | 6/2016 | Choi | F21V 13/10 |
| 9,448,127 B2* | 9/2016 | Cannard | B29C 66/7314 |
| 9,671,297 B2* | 6/2017 | Sibbett | G06F 3/045 |
| 10,590,296 B2* | 3/2020 | Lanceros Mendez | C09D 11/52 |
| 10,605,680 B2* | 3/2020 | Sun | G06F 3/0443 |
| 10,641,666 B2* | 5/2020 | Kim | D03D 1/0088 |

(Continued)

FOREIGN PATENT DOCUMENTS

CN   102207415 A   10/2011

OTHER PUBLICATIONS

Office Action of CN 202110540534.3 issued from the State Intellectual Property Office of the People's Republic of China dated May 10, 2023.

*Primary Examiner* — Tran M. Tran
(74) *Attorney, Agent, or Firm* — S&F/WEHRW

(57) ABSTRACT

The present disclosure provides a flexible pressure sensor array and method for fabricating the same. The pressure sensor array comprises a pressure-sensing substrate, top electrodes and bottom electrodes. The pressure-sensing substrate comprises a piezoresistive material, a fabric and pressure-sensing columns. The top electrodes and the bottom electrodes are attached to the pressure-sensing columns. The pressure sensor array is ultra-flexible and conforms to 3-dimensional surface for pressure monitoring.

17 Claims, 9 Drawing Sheets

(56) References Cited

U.S. PATENT DOCUMENTS

| | | | |
|---|---|---|---|
| 10,908,034 B2* | 2/2021 | Moriura | B62D 1/06 |
| 10,934,639 B2* | 3/2021 | Horter | G01L 1/146 |
| 10,935,445 B2* | 3/2021 | Bamunuarachchi | H01H 9/04 |
| 11,150,147 B2* | 10/2021 | Horter | D03D 1/00 |
| 11,274,393 B2* | 3/2022 | Aitchison | D06N 3/042 |
| 11,330,711 B2* | 5/2022 | Edmundson | H05K 1/0313 |
| 11,617,537 B2* | 4/2023 | Sarrafzadeh | A61B 5/7278 |
| | | | 702/41 |
| 2015/0294756 A1* | 10/2015 | Ben Shalom | G01L 1/246 |
| | | | 28/169 |
| 2017/0165941 A1* | 6/2017 | Li | C04B 28/08 |
| 2017/0234673 A1* | 8/2017 | Sibbett | G01L 1/205 |
| | | | 73/777 |
| 2019/0072440 A1* | 3/2019 | Menon | D03D 1/0088 |
| 2019/0218333 A1 | 7/2019 | Xu et al. | |
| 2021/0048358 A1* | 2/2021 | Huang | G01L 1/205 |
| 2021/0223119 A1* | 7/2021 | Moriura | G01L 5/22 |
| 2021/0318188 A1* | 10/2021 | Uragami | G01L 1/144 |
| 2022/0244112 A1* | 8/2022 | Matsumoto | G01L 1/146 |
| 2022/0252472 A1* | 8/2022 | Kim | G01L 1/205 |

\* cited by examiner

FLEXIBLE PRESSURE SENSOR ARRAY AND METHOD FOR FABRICATING THE SAME

CROSS-REFERENCE TO RELATED APPLICATIONS

This application claims the benefit of U.S. Provisional Patent Application No. 62/704,769, filed on May 28, 2020, which is incorporated by reference herein in its entirety.

TECHNICAL FIELD

The present disclosure relates to a pressure sensor array, more particularly, a flexible pressure sensor array and method for fabricating the same.

BACKGROUND

Wearable and light-weighted electronics are becoming more and more desirable in human life. Traditional tactile sensors are rigid and in fixed sizes and shapes. Printed pressure sensors on plastic foils such as polyethylene terephthalate (PET) and polyimide (PI) have been conventionally developed. These printed sensor arrays are flexible, but suffer reliability issues when they are applied on soft surface, e.g., chair mat and mattress. The printed silver electrodes and pressure sensitive material may crack when the sensor array is twisted or flexed, especially when the sensor is placed on a soft surface. The plastics foil substrate is flexible, but is difficult to conform to a three dimensional (3D) object with curved surface.

A need therefore exists for a flexible pressure sensor array that eliminates or at least diminishes the disadvantages and problems described above.

SUMMARY

Provided herein is a pressure sensor array comprising: a pressure-sensing substrate comprising: a piezoresistive material; a fabric divided into a plurality of filling portions and a non-filling portion, the plurality of filling portions of the fabric being separated with each other by the non-filling portion of the fabric, the non-filling portion of the fabric being not filled with the piezoresistive material; and a plurality of pressure-sensing columns electrically separated with each other by the non-filling portion of the fabric, each pressure-sensing column comprising a respective filling portion of the fabric and the piezoresistive material, the respective filling portion of the fabric being filled with the piezoresistive material, each pressure-sensing column having a top column surface and a bottom column surface.

In certain embodiments, the pressure sensor array further comprises: a plurality of top electrodes, each top electrode electrically connecting to one or more respective top column surfaces; and a plurality of bottom electrodes, each bottom electrode electrically connecting to one or more respective bottom column surfaces.

In certain embodiments, each top electrode is stitched to the pressure-sensing substrate to be periodically attached to a respective top column surface and a bottom surface of the non-filling portion of the fabric; and each bottom electrode is stitched to the pressure-sensing substrate to be periodically attached to a respective bottom column surface and a top surface of the non-filling portion of the fabric.

In certain embodiments, the pressure sensor array further comprises a top adhesive tape and a bottom adhesive tape, wherein each top electrode is attached to the one or more respective top column surfaces, the top adhesive tape adheres to each top electrode and a top surface of the non-filling portion of the fabric; and each bottom electrode is attached the one or more respective bottom column surfaces, the bottom adhesive tape adheres to each bottom electrode and a bottom surface of the non-filling portion of the fabric.

In certain embodiments, each top electrode is fixed to a top surface of the non-filling portion of the fabric by glue; and each bottom electrode is fixed to a bottom surface of the non-filling portion of the fabric by glue.

In certain embodiments, the pressure sensor array further comprises a plurality of top plastic covers and a plurality of bottom plastic covers, wherein each top plastic cover is located above a respective top column surface and a respective top electrode, a top surface of the non-filling portion of the fabric and the plastic cover being stuck together by glue; and each bottom plastic cover is located below a respective bottom column surface and a respective bottom electrode, a bottom surface of the non-filling portion of the fabric and the bottom plastic cover being stuck together by glue.

In certain embodiments, the plurality of top electrodes is aligned on the pressure-sensing substrate in one or more rows; and the plurality of bottom electrodes is aligned on the pressure-sensing substrate in one or more columns.

In certain embodiments, each top electrode is a first metal-coated yarn; and each bottom electrode is a second metal-coated yarn.

In certain embodiments, each of the first metal-coated yarn and the second metal-coated yarn is a silver-coated yarn, stainless steel-coated yarn, or a copper-coated yarn.

In certain embodiments, the pressure sensor array further comprises: a plurality of row electrodes, each row electrode being stitched to the pressure-sensing substrate to be periodically attached to a top column surface of a first pressure-sensing column and a bottom column surface of a second pressure-sensing column in row; and a plurality of column electrodes, each column electrode being stitched to the pressure-sensing substrate to be periodically attached to a top column surface of a first pressure-sensing column and a bottom column surface of a second pressure-sensing column in column.

In certain embodiments, the fabric is a cotton fabric or a blended fabric.

In certain embodiments, each pressure sensing column has a cross section being circular, square or rectangular, and a width between 1 mm and 10 mm.

In certain embodiments, the piezoresistive material comprises a conductive material and a polymer, the polymer binding the conductive material to fibers of the fabric.

In certain embodiments, the conductive material is metal particles or a conductive carbon material.

In certain embodiments, the metal particles are made of silver or copper; and the conductive carbon material is carbon black, carbon nanotubes, graphene, graphite, or a combination thereof.

In certain embodiments, the polymer is thermoplastic polyurethane (TPU), polyurethane (PU), phenoxy resin, polyacid, polyacrylic acid, polyacrylateand N,N'-dimethylol-4,5-dihydroxyethylene urea (DMDHEU) resin, poly(vinyl alcohol) (PVA), or polyethylene glycol (PEG).

Provided herein is a method for fabricating a pressure sensor array comprising:

a) providing a fabric divided into a plurality of filling portions and a non-filling portion;

b) placing a mold having a plurality of holes on a first surface of the fabric such that the plurality of filling portions of the fabric is exposed to the plurality of holes;

c) spraying a piezoresistive ink into the plurality of holes such that the plurality of filling portions of the fabric is soaked with the piezoresistive ink via the first surface thereby forming a partially piezoresistive ink-soaked fabric;

d) optionally, placing the mold on a second surface of the fabric and spraying the piezoresistive ink into the plurality of holes such that the plurality of filling portions of the fabric is soaked with the piezoresistive ink via the second surface thereby forming the partially piezoresistive ink-soaked fabric;

e) curing the piezoresistive ink in the partially piezoresistive ink-soaked fabric such that each filling portion of the fabric is filled with a piezoresistive material formed from the piezoresistive ink thereby forming a pressure-sensing substrate comprising a plurality of pressure-sensing columns electrically separated with each other by the non-filling portion of the fabric, each pressure-sensing column having a top column surface and a bottom column surface;

f) connecting each top electrode of a plurality of top electrodes to one or more respective top column surfaces; and g) connecting each bottom electrode of a plurality of bottom electrodes to one or more respective bottom column surfaces thereby forming the flexible pressure sensor array.

In certain embodiments, the piezoresistive ink comprises a polymer, a conductive material and a solvent.

In certain embodiments, the polymer has a concentration between 1% and 10% by weight, the conductive material has a concentration between 0.1% and 2% by weight and the solvent has a concentration between 90% and 95% by weight.

Provided herein is a pressure mapping system comprising: a pressure sensor array described above; an electrical resistance meter for measuring electrical resistance of each pressure sensor of the pressure sensor array; and a computer for imaging a pressure distribution profile based on the measured electrical resistance of each pressure senor.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Skilled artisans will appreciate that elements in the figures are illustrated for simplicity and clarity and have not necessarily been depicted to scale.

DETAILED DESCRIPTION OF THE INVENTION

The present disclosure provides a pressure sensor array for pressure mapping and a method for fabricating the same.

According to certain embodiments of the present disclosure, a pressure sensor array is made of a single layer of cotton fabric embroidered with conductive yarns and treated at specific spots with pressure sensor composition having a polymer, a conductive carbon material and a solvent. To prepare a piezoresistive ink which is capable of being sprayed onto the cotton fabric, polymers with good affinity to cotton are selected to bind the conductive carbon material to the fabric. The piezoresistive ink is sprayed onto the cotton fabric with a pre-designed mold (or mask). The mold determines the size of each pressure sensor and the resolution of the pressure sensor array. To get a uniform coating, it is better to spray both side of the cotton fabric by sandwiching the cotton fabric between two identical stencil molds. After the spraying, the treated cotton fabric is cured. Top row electrodes and bottom column electrodes are formed by stitching the conductive yarns to both sides of the cotton fabric. The stitching is arranged in a way that the crossing point does not incur short circuit between top and bottom conduction paths. The cross point of the top row electrode and the bottom column electrode defines the pixel points.

Figure 1:
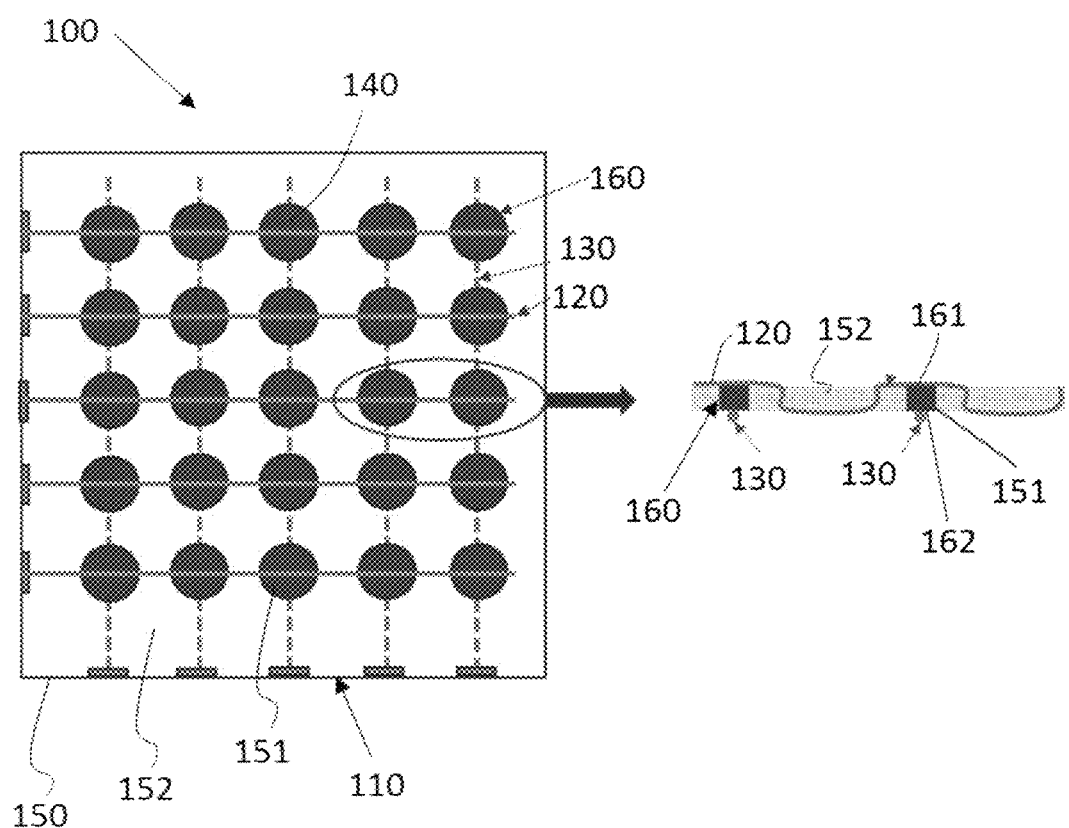
FIG. 1 shows a plan view and a cross-sectional view of a flexible pressure sensor array according to certain embodiments.

FIG. 1 shows a plan view and a cross-sectional view of a flexible pressure sensor array according to certain embodiments. The flexible pressure sensor array 100 comprises a pressure-sensing substrate 110, top flexible electrodes 120 and bottom flexible electrodes 130. The pressure-sensing substrate 110 comprises a piezoresistive material 140, a fabric 150, and a plurality of pressure-sensing columns 160. The fabric 150 is divided into portions comprising a plurality of filling portions 151 of the fabric 150 and a non-filling portion 152 of the fabric 150, the plurality of filling portions 151 is separated with each other by the non-filling portion 152, the non-filling portion 152 is not filled with the piezoresistive material 140 and thus contains fibers of the fabric 150 only such that the flexibility of the pressure sensory array 100 is not affected. The plurality of pressure-sensing columns 160 are electrically separated with each other by the non-filling portion 152 such that cross interference among different pressure sensors can be avoided, each pressure-sensing column 160 comprises a respective filling portion 151 and the piezoresistive material 140, the respective filling portion 151 is filled with the piezoresistive material 140, which is attached to fibers in the filing portion 151, each pressure-sensing column 160 has a top column surface 161 and a bottom column surface 162. Each top electrode 120 electrically connects to respective top column surfaces 161, and each bottom electrode 130 electrically connects to respective bottom column surfaces 162.

In this embodiment, each top electrode 120 is stitched to the pressure-sensing substrate 110 to be periodically attached to the top column surface 161 and a bottom surface of the non-filling portion 152. Each bottom electrode 120 is stitched to the pressure-sensing substrate 110 to be periodically attached to the bottom column surface 161 and a top surface of the non-filling portion 152.

In this embodiment, the plurality of top electrodes 120 is aligned on the pressure-sensing substrate 110 in rows; and the plurality of bottom electrodes 130 is aligned on the pressure-sensing substrate 110 in columns.

In certain embodiments, the pressure sensor array has a sensor pixel density between 1 and 25 sensors/in$^2$ or between 5 and 15 sensors/in$^2$.

In certain embodiments, the fabric is a cotton fabric or a blended fabric. The blended fabric may comprise 5-10% polyester cotton or 3-5% LYCRA cotton for elasticity.

In certain embodiments, the fabric has a thread count between 20 and 60 or between 35 and 45; and fabric has a density between 150 g/m$^3$ and 260 g/m$^3$ or between 190 g/m$^3$ and 210 g/m$^3$.

In certain embodiments, each pressure sensing column has a cross section being circular, square or rectangular.

In certain embodiments, each pressure sensing column has a width between 1 mm and 10 mm.

In certain embodiments, a distance between two consecutive pressure sensing columns is between 5 mm and 20 mm.

In certain embodiments, the piezoresistive material comprises a conductive material and a polymer, and the polymer binds the conductive material to fibers of the fabric.

In certain embodiments, the conductive material is metal particles or a conductive carbon material.

In certain embodiments, the metal particles are made of silver or copper; and the conductive carbon material is carbon black, carbon nanotubes, graphene, graphite, or a combination thereof.

In certain embodiments, the polymer is the polymer is thermoplastic polyurethane (TPU), polyurethane (PU), phenoxy resin, polyacid, polyacrylic acid, polyacrylate and N,N'-dimethylol-4,5-dihydroxyethylene urea (DMDHEU) resin, poly(vinyl alcohol) (PVA), or polyethylene glycol (PEG). The above polymers can bind the conductive material to fibers of the fabric without affecting the softness of the fabric.

In certain embodiments, each top electrode is made of a metal-coated yarn or a conductive yarn; and each bottom electrode is made of a metal-coated yarn or a conductive yarn. The metal-coated yarn may have an electrical resistance below 200 Ohm per meter.

In certain embodiments, the metal-coated yarn is a silver-coated yarn, stainless steel-coated yarn, or a copper-coated yarn.

In certain embodiments, each top electrode has a diameter between 0.3 mm and 0.5 mm; and each bottom electrode has a diameter between 0.3 mm and 0.5 mm.

Figure 2:
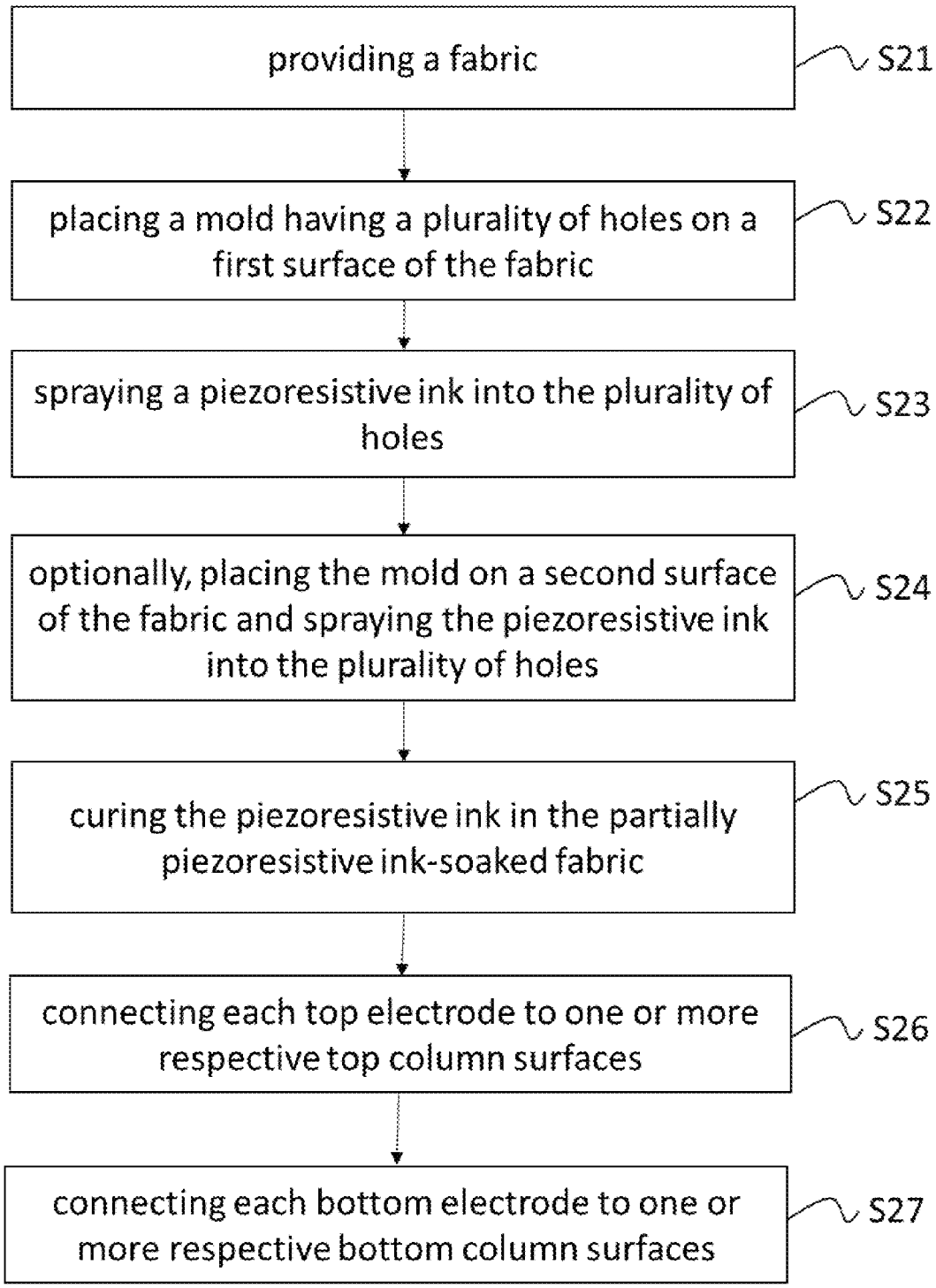
FIG. 2 is flow chart depicting a method for fabrication of a flexible pressure sensor array according to certain embodiments.

FIG. 2 is flow chart depicting a method for fabricating a flexible pressure sensor array according to certain embodiments. In step S21, a fabric comprising a plurality of filling portions of the fabric and a non-filling portion of the fabric is provided. In step S22, a mold (or mask) having a plurality of holes is placed on a first surface of the fabric such that the plurality of filling portions of the fabric is exposed to the plurality of holes. In step S23, a piezoresistive ink is sprayed into the plurality of holes such that the plurality of filling portions of the fabric is soaked with the piezoresistive ink via the first surface thereby forming a partially piezoresistive ink-soaked fabric. In step S24, optionally, the mold is placed on a second surface of the fabric and the piezoresistive ink is sprayed into the plurality of holes such that the plurality of filling portions of the fabric is soaked with the piezoresistive ink via the second surface thereby forming the partially piezoresistive ink-soaked fabric. In step S25, the piezoresistive ink in the partially piezoresistive ink-soaked fabric is cured such that each filling portion of the fabric is filled with a piezoresistive material formed from the piezoresistive ink thereby forming a pressure-sensing substrate comprising a plurality of pressure-sensing columns electrically separated with each other by the non-filling portion of the fabric, each pressure-sensing column having a top column surface and a bottom column surface. In step 26, each top electrode of a plurality of top electrodes is connected to one or more respective top column surfaces. In step S27, each bottom electrode of a plurality of bottom electrodes is connected to one or more respective bottom column surfaces thereby forming the flexible pressure sensor array.

In certain embodiments, each hole of the mold has a circular shape, a square shape or a rectangular shape. The mold can be made of a metal alloy, copper, aluminum or stainless steel.

In certain embodiments, the piezoresistive ink comprises a polymer, a conductive material and a solvent.

In certain embodiments, the conductive material is metal particles or a conductive carbon material.

In certain embodiments, the metal particles are made of silver or copper; and the conductive carbon material is carbon black, carbon nanotubes, graphene, graphite, or a combination thereof.

In certain embodiments, the polymer is TPU, PU, phenoxy resin, polyacid, polyacrylic acid, polyacrylate and DMDHEU resin, PVA, or PEG.

In certain embodiments, the solvent is a ketone (e,g, methyl ethyl ketone (MEK) and isophorone), an ester (e.g., ethyl acetate (EA), dibasic ester (DBE), 2-butoxyethyl acetate and and 2-methoxyethyl acetate), or a diol ether (e.g., 2-butoxyethanol).

In certain embodiments, the polymer has a concentration between 1% and 10% by weight, the conductive material has a concentration between 0.1% and 2% by weight and the solvent has a concentration between 90% and 95% by weight.

In certain embodiments, the piezoresistive ink has a viscosity between 50 cp and 500 cp.

In certain embodiments, the spraying of the piezoresistive ink is performed by a programmable and automatic spraying machine for obtaining pressure sensors having homogeneous properties.

In certain embodiments, the spraying of the piezoresistive ink is performed with 2-5 times for improving sensor-to-sensor uniformity.

In certain embodiments, the piezoresistive ink in the partially piezoresistive ink-soaked fabric is cured at a temperature between 120° C. and 140° C. for 0.5-1.5 hr.

Figure 3A:
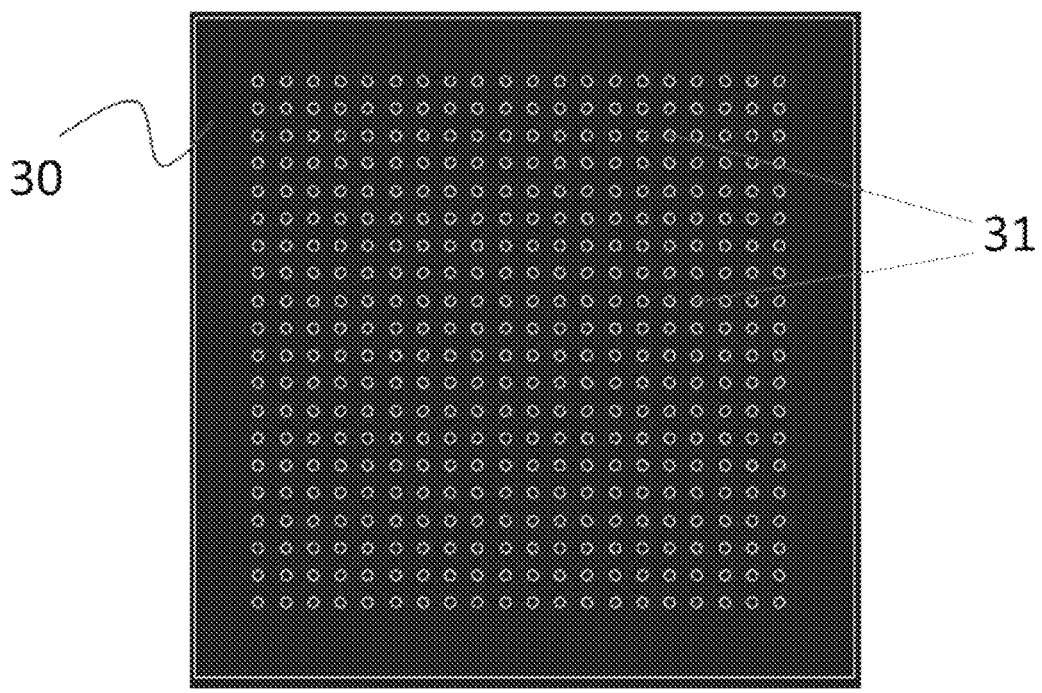
FIG. 3A is a schematic diagram showing a mold according to certain embodiments.
Figure 3B:
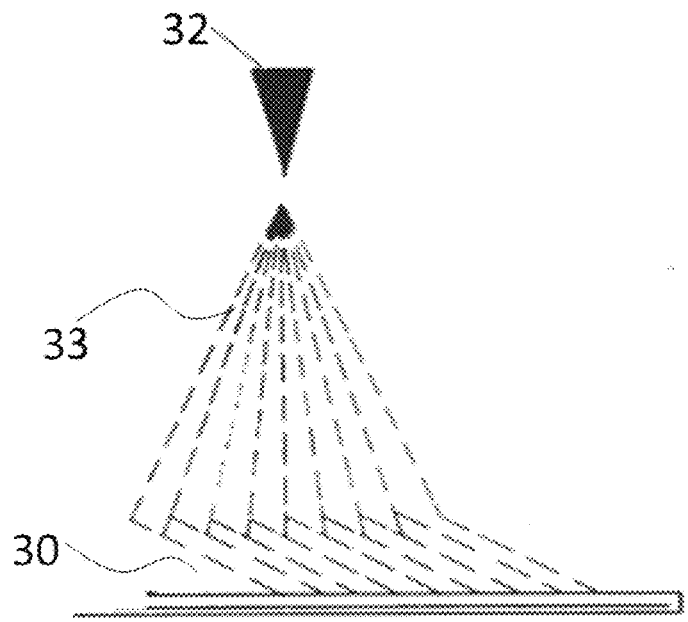
FIG. 3B is a schematic diagram showing a spraying machine for spraying a piezoresistive ink onto the mold according to certain embodiments.

FIG. 3A shows a mold according to certain embodiments. The mold 30 has a plurality of circular holes 31 for defining the filling portions of a fabric to obtain a designed sensor pattern. FIG. 3B shows a spraying machine 32 spraying a piezoresistive ink 33 onto the mold 30.

Figure 4A:
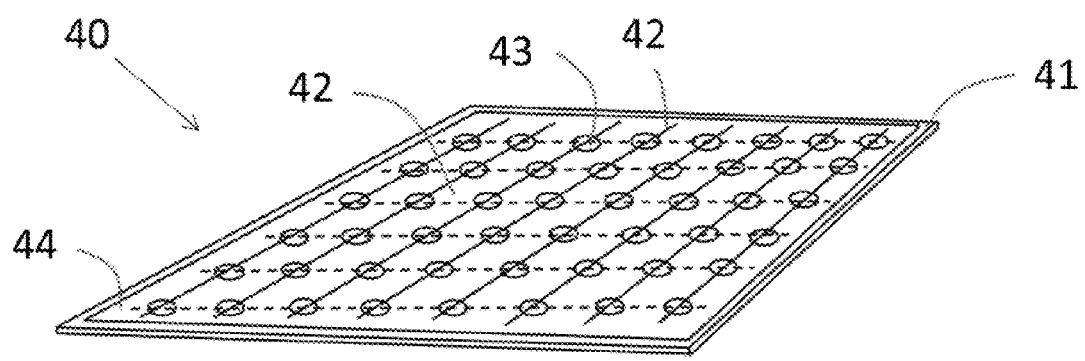
FIG. 4A shows an isometric view of a flexible pressure sensor array using adhesive plastic tapes to fix electrodes to a pressure-sensing substrate according to certain embodiments.
Figure 4B:
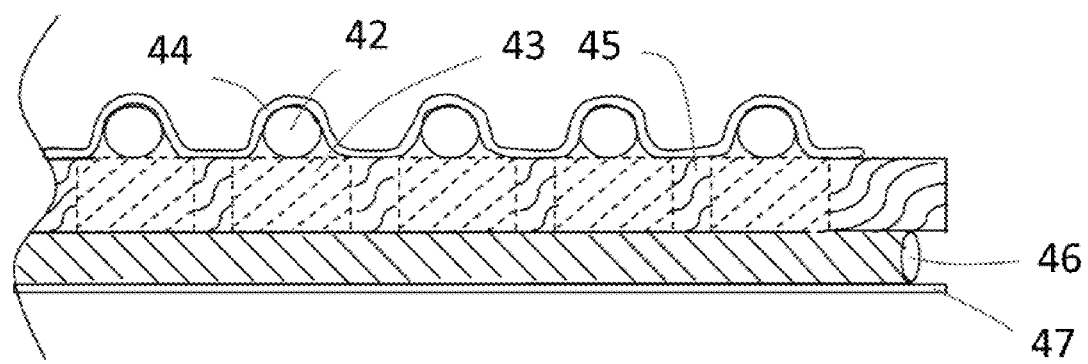
FIG. 4B shows a cross-sectional view of the flexible pressure sensor array of FIG. 4A.

FIGS. 4A and 4B depicts a flexible pressure sensor array 40 using adhesive plastic tapes to fix electrodes to a pressure-sensing substrate. Silver-coated yarns 42 are attached to the top surface of the pressure-sensing substrate 41 such that each silver-coated yarn 42 is attached to the top column surfaces of the respective pressure-sensing columns 43 in row. Then, an adhesive plastic tape 44 adheres on the silver-coated yarns 42 and the top surface of the non-filling portion 45 of the fabric to fix the silver-coated yarns 42 to the pressure-sensing substrate 41. Similarly, silver-coated yarns 46 are attached to the bottom surface of the pressure-sensing substrate 41 such that each silver-coated yarn 46 attached to the bottom column surfaces of the respective pressure-sensing columns 43 in column. Then, an adhesive plaster 47 adheres on the silver-coated yarns 46 and the bottom surface of the non-filling portion 45 of the fabric to fix the silver-coated yarns 46 to the pressure-sensing substrate 41.

Figure 5:
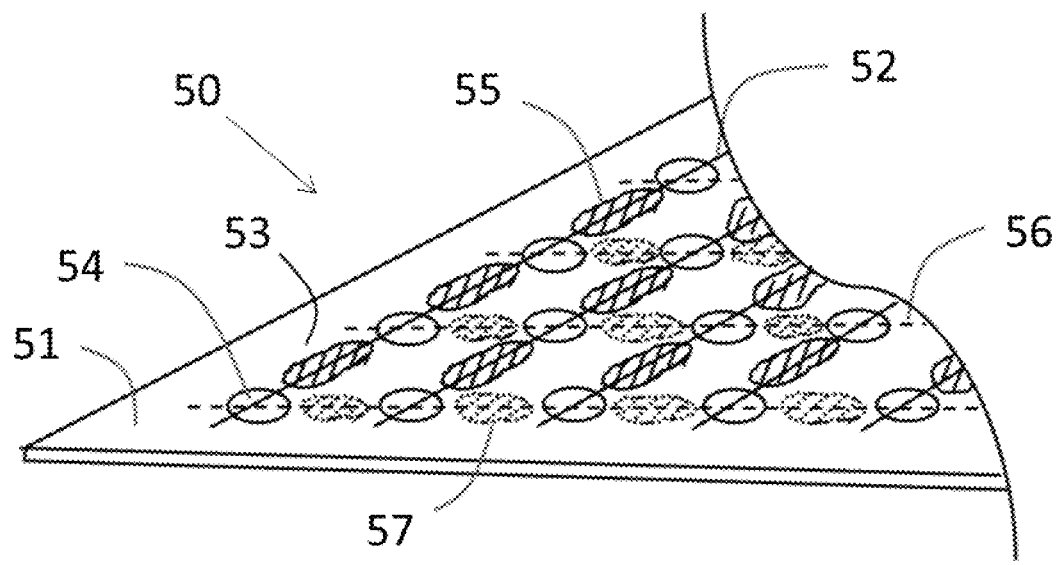
FIG. 5 shows an isometric view of a flexible pressure sensor array using glue to fix electrodes to a pressure-sensing substrate according to certain embodiments.

FIG. 5 depicts a flexible pressure sensor array 50 using glue to fix electrodes onto a pressure-sensing substrate. On the top surface of a pressure-sensing substrate 51, each silver-coated yarn 52 is fixed to the top surface of the non-filling portion 53 of the fabric between two pressure-sensing columns 54 by glue 55 in row. Similarly, on the bottom surface of the pressure-sensing substrate 51, each silver-coated yarn 56 is fixed to the bottom surface of the non-filling portion 53 between two pressure-sensing columns 54 by glue 57 in column.

Figure 6:
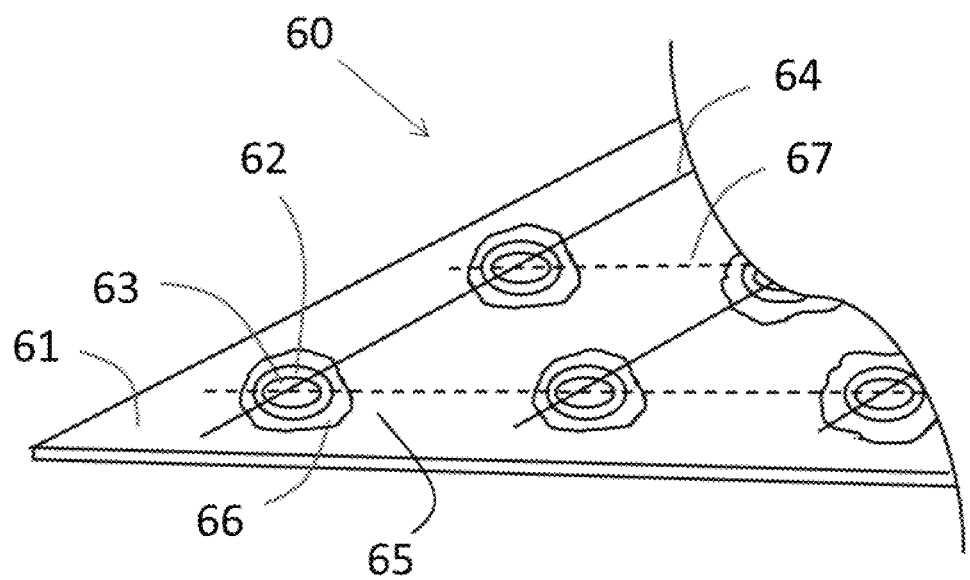
FIG. 6 shows an isometric view of a flexible pressure sensor array using glue and plastic cover to fix electrodes to a pressure-sensing substrate according to certain embodiments.

FIG. 6 depicts a flexible pressure sensor array 60 using glue and plastic covers to fix electrodes onto a pressure-sensing substrate. On the top surface of a pressure-sensing substrate 61, each plastic cover 62 is located above a respective pressure-sensing column 63 and a respective silver-coated yarn 64 for protecting the pressure-sensing column 63 and the silver-coated yarn 64, the top surface of the non-filling portion 65 and the plastic cover 62 are stuck together by glue 66 for preventing the glue 66 from affecting conductivity of the pressure-sensing column 63 and the silver-coated yarn 64. The silver-coated yarns 67 are fixed to the bottom surface of the pressure-sensing substrate 61 in the same way.

Figure 7A:
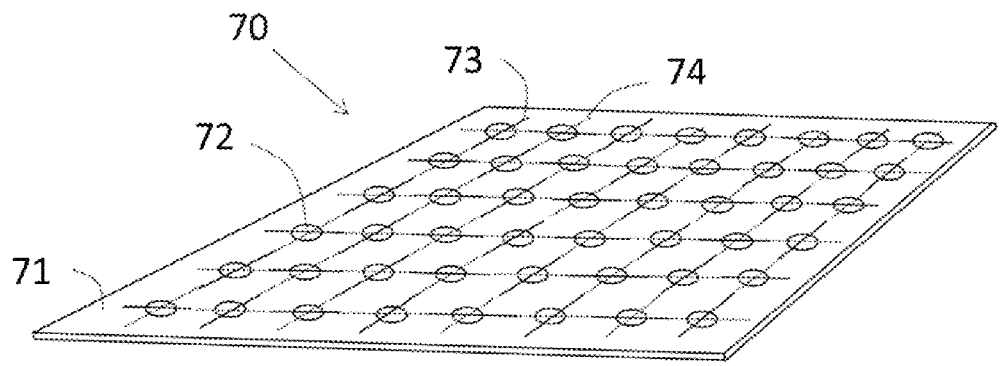
FIG. 7A shows an isometric view of a flexible pressure sensor array using stitching to fix electrodes to a pressure-sensing substrate according to certain embodiments.
Figure 7B:
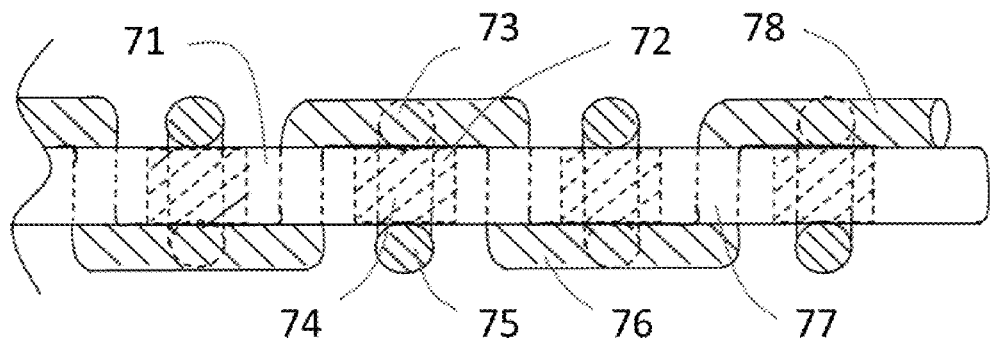
FIG. 7B shows a cross-sectional view of the flexible pressure sensor array of FIG. 7A.

FIGS. 7A and 7B depict a flexible pressure sensor array 70 using stitching to fix column electrodes and rod electrodes on a pressure-sensing substrate. A pressure-sensing substrate 71 has a plurality of pressure-sensing columns 72. Each column electrode (e.g., a silver-coated yarn) is stitched to the pressure sensing substrate 71 to periodically be attached to on a top column surface 73 of a pressure-sensing column, pass through a non-filling portion 74 of fabric and be attached to a bottom column surface 75 of the next pressure-sensing column in column. Similarly, each row electrode (e.g., a silver-coated yarn) is stitched to the pressure sensing substrate 71 to periodically be attached to a bottom column surface 76 of a pressure-sensing column, pass through a non-filling portion 77 of fabric and be attached to a top column surface 78 of the next pressure-sensing column in row.

Example 1

A piezoresistive nano-carbon ink being printed onto cotton or blended fabrics is prepared as follows.

A TPU polymer solution is prepared by: weighing 22 wt % TPU resin in DBE solvent in a glass bottle using the balance; putting the bottle on a hot plate to dissolve TPU resin in DBE (hot plate temperature: 120° C.) for 24 h to get 22% TPU solution. Then, 0.28 g VX72R nano carbon black and 5 g 22% TPU solution, 15 g DBE solvent are weighed, and the above paste is mixed using vacuum mixer (1000 rpm, 10 mins) to get the piezoresistive nano-carbon ink.

Example 2

A piezoresistive nano-carbon ink being printed to cotton or blended fabrics is prepared as follows.

A TPU polymer solution is prepared by: weighing 22 wt % TPU resin in DBE solvent in a glass bottle using the balance; putting the bottle on a hot plate to dissolve TPU resin in DBE (hot plate temperature: 120° C.) for 24 h to get 22% TPU solution. Then, 0.14 g VX72R nano carbon black and 5 g 22% TPU solution, 15 g DBE solvent are weighed, and the above paste is mixed using vacuum mixer (1000 rpm, 10 mins) to get the piezoresistive nano-carbon ink for different electrical resistance ranges.

Example 3

A piezoresistive nano-carbon ink being printed to cotton or blended fabrics is prepared as follows.

30 wt % phenoxy (PKHH) resin in 2-butoxyethyl acetate is weighed in a glass bottle using a balance, the bottle is put on the hot plate to dissolve PKHH resin in 2-butoxyethyl acetate (hot plate temperature: 120° C.) for 24 h to get the 30% wt phenoxy resin solution. Then, 0.2 g VX72R nano carbon black and 4 g 30% phenoxy resin solution, 15 g 2-butoxyethyl acetate solvent are weighed, and the above paste is mixed using vacuum mixer (1000 rpm, 10 mins) to get the piezoresistive nano-carbon.

Example 4

A piezoresistive nano-carbon ink being printed to cotton or blended fabrics is prepared as follows.

A polyacid solution is prepared by: weighing 30 wt % polyacid resin in DI water in a glass bottle using the balance; putting the bottle on a hot plate to dissolve under room temperature to get 30% polyacid resin solution. Then, 1.0 g polyaniline conductive polymer solution and 5 g 30% polyacid resin solution, 10 g DI water are weighed, and the above materials are mixed using vacuum mixer (1000 rpm, 10 mins) to get the piezoresistive ink.

Example 5

A piezoresistive nano-carbon ink being printed to cotton or blended fabrics is prepared as follows.

A DMDHEU solution is prepared by: weighing 30 wt % DMDHEU resin in DI water in a glass bottle using a balance; putting the bottle on ae hot plate to dissolve under room temperature to get 30% 2D resin solution. Then, 1.0 g polyaniline conductive polymer solution and 5 g 30% 2D resin solution, 10 g DI water are weighed, and the above materials are mixed using vacuum mixer (1000 rpm, 10 mins) to get the piezoresistive ink.

Figure 8A:
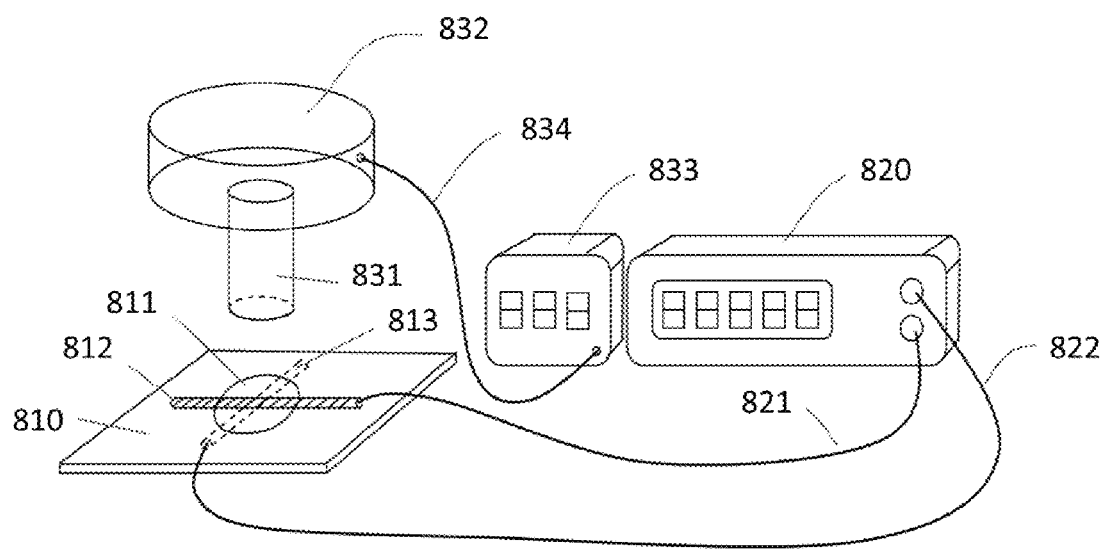
FIG. 8A is a schematic diagram depicting an experimental set-up for measuring electrical resistance of a pressure sensor of a flexible pressure sensor array according to certain embodiments.

FIG. 8A is a schematic diagram depicting an experimental set-up for measuring electrical resistance of a pressure sensor of a flexible pressure sensor array under different loading according to certain embodiments. A pressure sensory array 810 having a plurality of pressure sensors is provided. The pressure sensor includes a pressure-sensing column 811, a top electrode 812 and a bottom electrode 813, the top electrode 812 is attached to the top column surface of the pressure-sensing column 811 and the bottom electrode is attached to the bottom column surface of the pressure-sensing column 811. An electrical resistance meter 820 is connected to the top electrode 812 and the bottom electrode 813 by two conductive wires 821 and 822 respectively. A metal axle 831 for applying a loading to the pressure sensor is connected to a force sensor 832, which is connected to a force meter 833 by a signal wire 834.

Figure 8B:
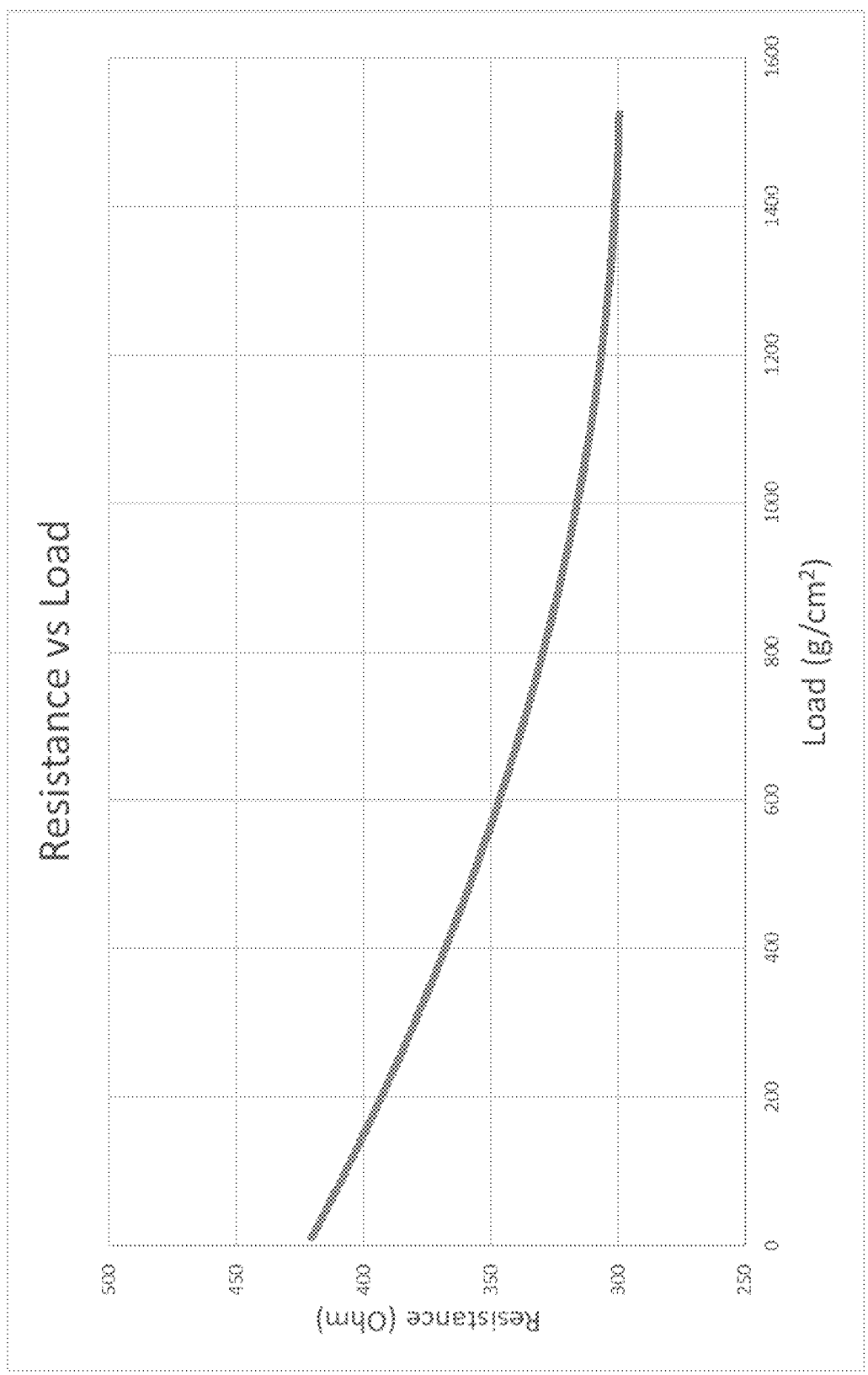
FIG. 8B shows a response curve of the pressure sensor of FIG. 8A.

FIG. 8B shows a response curve of the pressure sensor of FIG. 8A. The electrical resistance of the pressure sensor is dropped from 420 Ohm to 300 Ohm when the loading is increased from 0 g/cm$^3$ to 1500 g/cm$^3$.

The flexible pressure senor array described above is applicable for chair/bed mat for sitting/sleeping health monitoring, insole for gait analysis, compression stockings, or other wearable sensor applications.

Figure 9:
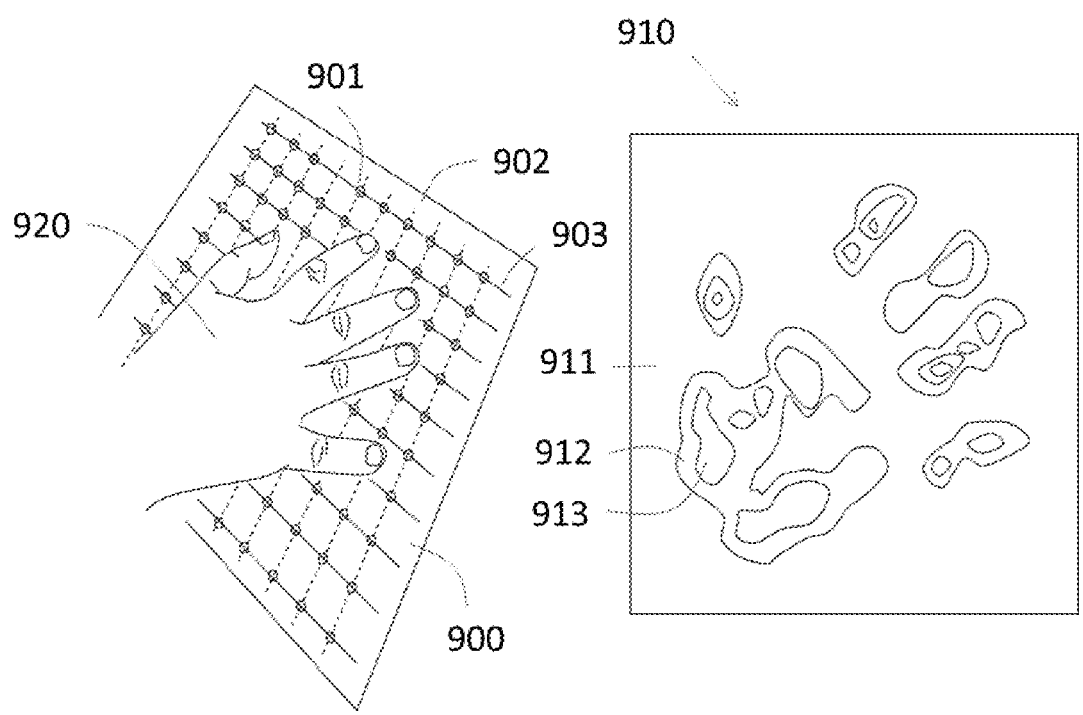
FIG. 9 shows a flexible pressure sensor array for checking hand pressure distribution according to certain embodiments.

FIG. 9 shows a pressure sensor array 900 for checking hand pressure distribution according to certain embodiments. The pressure sensor array 900 comprises a plurality of pressure-sensing columns 901, a plurality of vertical silver-coated yarns 902 on bottom and a plurality of horizontal silver-coated yarns 903 on top. A pressure distribution profile 910 of a hand 920 is determined by the pressure sensor array 900. A region 911 on the pressure distribution profile 910 represents no pressure applied herein and is filled with background color. A region 912 represents light pressure applied herein and is filled with a light color. A region 913 represents more pressure applied herein and is filled with a deeper color.

Figure 10:
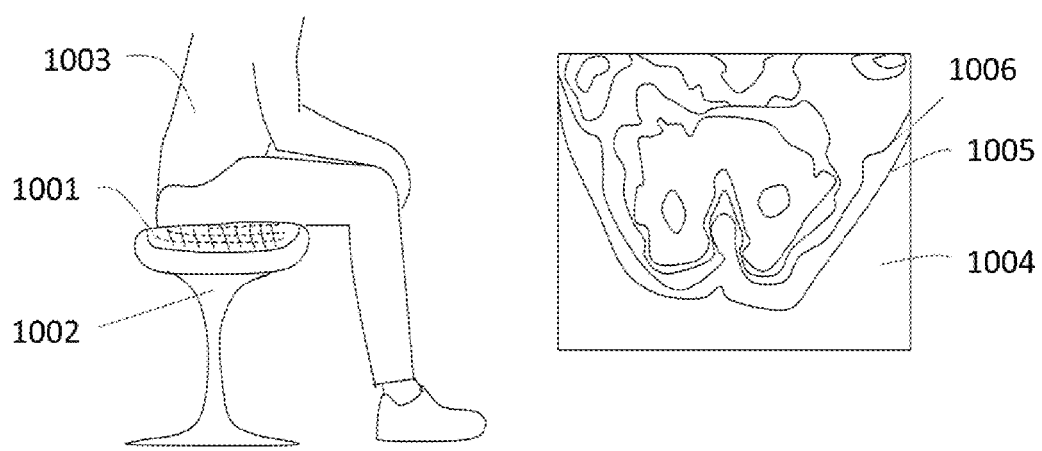
FIG. 10 shows a pressure sensor array for monitoring sitting posture according to certain embodiments.

FIG. 10 shows a pressure sensor array 1001 for monitoring a sitting posture according to certain embodiments. The pressure sensor array 1001 is placed on a chair 1002 for monitoring a sitting posture of a human 1003. The corresponding pressure distribution profile is shown in an image 1004 comprising different pressure lines 1005 and 1006.

Figure 11:
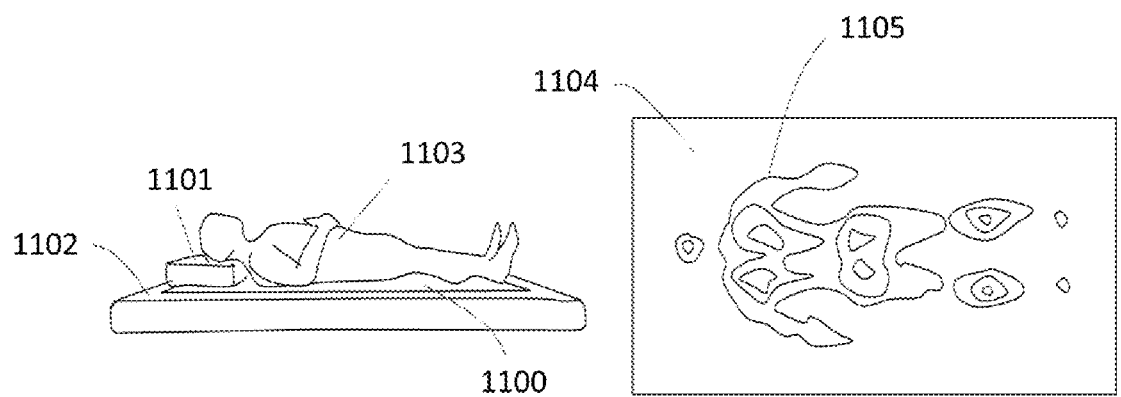
FIG. 11 shows a pressure sensor array pad for monitoring sleeping posture according to certain embodiments.

FIG. 11 shows a pressure sensor array pad 1100 for monitoring sleeping posture according to certain embodiments. The pressure sensor array pad 1100 can be used for health monitoring or mattress development. A pillow 1101 is placed on a mattress 1102. The pressure sensor array pad 1100 is placed on the pillow 1101 and the mattress 1102 for monitoring sleeping posture of a human 1103. The corresponding pressure distribution profile is shown in an image 1104 having different pressure lines 1105.

Thus, it can be seen that an improved flexible pressure sensor array has been disclosed which eliminates or at least diminishes the disadvantages and problems associated with prior art processes. The pressure sensor array is ultra-flexible and conforms to 3-dimensional surface for pressure monitoring. The electrodes formed with conductive yarns provide high reliability. The fabrication of the pressure sensor array with stitching/adhesion and spraying provides low fabrication cost.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A pressure sensor array comprising:
   a pressure-sensing substrate comprising:
   a piezoresistive material;
   a fabric divided into a plurality of filling portions and a non-filling portion, the plurality of filling portions of the fabric being separated with each other by the non-filling portion of the fabric, the non-filling portion of the fabric being not filled with the piezoresistive material;
   a plurality of pressure-sensing columns electrically separated with each other by the non-filling portion of the fabric, each pressure-sensing column comprising a respective filling portion of the fabric and the piezoresistive material, the respective filling portion of the fabric being filled with the piezoresistive material, each pressure-sensing column having a top column surface and a bottom column surface;
   a plurality of top electrodes aligned on the pressure-sensing substrate in rows from a planar surface view of the pressure-sensing substrate, each top electrode electrically connecting to one or more respective top column surfaces of the pressure-sensing columns and stitched to the pressure-sensing substrate to be periodically attached to a respective top column surface of the pressure-sensing column and a bottom surface of the non-filling portion of the fabric; and
   a plurality of bottom electrodes aligned on the pressure-sensing substrate in columns from the planar surface view of the pressure-sensing substrate, each bottom electrode electrically connecting to one or more respective bottom column surfaces of the pressure-sensing columns and stitched to the pressure-sensing substrate to be periodically attached to a respective bottom column surface of the pressure-sensing column and a top surface of the non-filling portion of the fabric,
   the plurality of top electrodes and the plurality of bottom electrodes being stitched in a way that each cross point between the top electrodes and the bottom electrodes does not incur short circuit but only defines pixel point from the planar surface view of the pressure-sensing substrate.

2. The pressure sensor array of claim 1 further comprising a top adhesive tape and a bottom adhesive tape, wherein each top electrode is attached to the one or more respective top column surfaces, the top adhesive tape adheres to each top electrode and a top surface of the non-filling portion of the fabric; and each bottom electrode is attached to the one or more respective bottom column suffices, the bottom adhesive tape adheres to each bottom electrode and a bottom surface of the non-filling portion of the fabric.

3. The pressure sensor array of claim 1, wherein each top electrode is fixed to a top surface of the non-filling portion of the fabric by, glue; and each bottom electrode is fixed to a bottom surface of the non-filling portion of the fabric by glue.

4. The pressure sensor array of claim 1 further comprising a plurality of top plastic covers and a plurality of bottom plastic covers, wherein each top plastic cover is located above a respective top column surface and a respective top electrode, a top surface of the non-filling, portion of the fabric and the plastic cover being stuck together by glue; and each bottom plastic cover is located below a respective bottom column surface and a respective bottom electrode, a bottom surface of the non-filling portion of the fabric and the bottom plastic cover being stuck together by glue.

5. The pressure sensor array of claim 1, wherein each top electrode is a first metal-coated yarn; and each bottom electrode is a second metal-coated yarn.

6. The pressure sensor array of claim 5, wherein each of the first metal-coated yarn and the second metal-coated yarn is a silver-coated yarn, stainless steel-coated yarn, or a copper-coated yarn.

7. The pressure sensor array of claim 1, wherein
each of the top electrodes is stitched to the pressure-sensing substrate to be periodically attached to a top column surface of a first pressure-sensing column and a bottom column surface of a second pressure-sensing column in the same row from the planar surface view of the pressure-sensing substrate; and
each of the bottom electrodes is stitched to the pressure-sensing substrate to be periodically attached to a top column surface of a first pressure-sensing column and a bottom column surface of a second pressure-sensing column in the same column from the planar surface view of the pressure-sensing substrate.

8. The pressure sensor array of claim 1, wherein the fabric is a cotton fabric or a blended fabric.

9. The pressure sensor array of claim 1, wherein each pressure sensing column from the planar surface view of the pressure-sensing substrate has a cross section being circular, square or rectangular, and a width between 1 mm and 10 mm.

10. The pressure sensor array of claim 1, wherein the piezoresistive material comprises a conductive material and a polymer, the polymer binding the conductive material to fibers of the fabric.

11. The pressure sensor array of claim 10, wherein the conductive material is metal particles or a conductive carbon material.

12. The pressure sensor array of claim 11, wherein the metal particles are made of silver or copper; and the conductive carbon material is carbon black, carbon nanotubes, grapheme, graphite, or a combination thereof.

13. The pressure sensor array of claim 10, wherein the polymer is thermoplastic polyurethane (TPU), polyurethane (PU), phenoxy resin, polyacid, polyacrylic acid, polyacrylate, N,N-dimethylol-4,5-dihydroxyethylene urea (DMD-HEU) resin, poly(vinyl alcohol) (PVA), or polyethylene glycol (PEG).

14. A pressure mapping system comprising:
a pressure sensor array of claim 1;
an electrical resistance meter for measuring electrical resistance of each pressure sensor of the pressure sensor array; and
a computer for imaging a pressure distribution profile based on the measured electrical resistance of each pressure senor.

15. A method for fabricating the pressure sensor array according to claim 7, the method comprising:
a) providing a fabric divided into a plurality of filling portions and a non-filling portion;
b) placing a mold having a plurality of holes on a first surface of the fabric such that the plurality of filling portions of the fabric is exposed to the plurality of holes;
c) spraying a piezoresistive ink into the plurality of holes such that the plurality of filling portions of the fabric is soaked with the piezoresistive ink via the first surface thereby forming a partially piezoresistive ink-soaked fabric;
d) optionally, placing the mold on a second surface of the fabric and spraying the piezoresistive ink into the plurality of holes such that the plurality of filling portions of the fabric is soaked with the piezoresistive ink via the second surface thereby forming the partially piezoresistive ink-soaked fabric;
e) curing the piezoresistive ink in the partially piezoresistive ink-soaked fabric such that each filling portion of the fabric is filled with a piezoresistive material formed from the piezoresistive ink thereby forming a pressure-sensing substrate comprising a plurality of pressure-sensing columns electrically separated with each other by the non-filling portion of the fabric, each pressure-sensing column having a top column surface and a bottom column surface;
f) connecting each top electrode of a plurality of top electrodes to one or more respective top column surfaces of the pressure-sensing columns by stitching to periodically attach each of the top electrodes on a top column surface of a pressure-sensing column, pass through the non-filling portion, and then attach the top electrode on a bottom column surface of a subsequent pressure-sensing column in the same row from the planar surface view of the pressure-sensing substrate; and
g) connecting each bottom electrode of a plurality of bottom electrodes to one or more respective bottom column surfaces of the pressure-sensing columns by stitching to periodically attach each of the bottom electrodes on a bottom column surface of a pressure-sensing column, pass through the non-filling portion, and then attach the bottom electrode on a top column surface of a subsequent pressure-sensing column in the same column from the planar surface view of the pressure-sensing substrate, thereby forming the flexible pressure sensor array,
said stitching of the top electrodes in step (f) and said stitching of the bottom electrodes in step (g) being in a way that each cross point between the top electrodes and the bottom electrodes does not incur short circuit but only defines pixel point from the planar surface view of the pressure-sensing substrate, the pixel point being a spot where the piezoresistive ink is sprayed into each of the plurality of the holes.

16. The method of claim 15, wherein the piezoresistive ink comprises a polymer, a conductive material and a solvent.

17. The method of claim 16, wherein the polymer has a concentration between 1% and 10% by weight, the conductive material has a concentration between 0.1% and 2% by weight and the solvent has a concentration between 90% and 95% by weight.

\* \* \* \* \*